(12) United States Patent
Kalb et al.

(10) Patent No.: US 9,868,635 B2
(45) Date of Patent: Jan. 16, 2018

(54) USE OF AN IONIC LIQUID FOR STORING HYDROGEN

(71) Applicant: VTU HOLDING GMBH, Grambach (AT)

(72) Inventors: Roland Kalb, Sinabelkirchen (AT); Alexander Kraynov, Graz (AT)

(73) Assignee: PROIONIC GMBH, Grambach (AT)

( * ) Notice: Subject to any disclaimer, the term of this patent is extended or adjusted under 35 U.S.C. 154(b) by 198 days.

(21) Appl. No.: 14/371,904

(22) PCT Filed: Dec. 20, 2012

(86) PCT No.: PCT/EP2012/076305
§ 371 (c)(1),
(2) Date: Jul. 11, 2014

(87) PCT Pub. No.: WO2013/113452
PCT Pub. Date: Aug. 8, 2013

(65) Prior Publication Data
US 2015/0048275 A1 Feb. 19, 2015

(30) Foreign Application Priority Data
Feb. 2, 2012 (EP) .................................. 12153677

(51) Int. Cl.
*C07D 295/037* (2006.01)
*C07F 9/54* (2006.01)
(Continued)

(52) U.S. Cl.
CPC ............ *C01B 3/0015* (2013.01); *C01B 3/001* (2013.01); *C01B 3/065* (2013.01); *C07C 211/63* (2013.01);
(Continued)

(58) Field of Classification Search
CPC ....... C01B 3/0015; C01B 3/065; C01B 3/001; C01B 6/23; C07D 295/037; C07F 9/5407;
(Continued)

(56) References Cited

U.S. PATENT DOCUMENTS 6,002,044 A 12/1999 Yamada et al.
6,489,374 B1 12/2002 Baudin
(Continued)

FOREIGN PATENT DOCUMENTS

CN 101519188 9/2009
CN 101654223 2/2010
(Continued)

OTHER PUBLICATIONS

Bürchner, Mara; Erle, Anna M.T.; Scherer, Harald; Krossing, Ingo; "Synthesis and Characterization of Boranate Ionic Liquids (BILs)" Chemistry, a European Journal (2012), in press; DOI: 10.1002/chem.2011102460.
(Continued)

*Primary Examiner* — Peter F Godenschwager
*Assistant Examiner* — Andrew J. Oyer
(74) *Attorney, Agent, or Firm* — Workman Nydegger

(57) ABSTRACT

Method of storing hydrogen by forming a first ionic liquid by inducing a borohydride in a second ionic liquid comprising a cation and an anion comprising borate, and forming the second ionic liquid by releasing the hydrogen out of the first ionic liquid by using water and/or a catalyst, which method is characterized in that the first and the second ionic liquid are both water miscible and the second ionic liquid is separated, particularly is salted out, from solution in water by adding a separation inducer; certain ionic liquids for storing and releasing hydrogen comprising a borohydride or for preparing a ionic liquid for storing and releasing hydrogen comprising a borate; and a process for preparing ionic
(Continued)

liquids for storing and releasing hydrogen comprising a borohydride.

20 Claims, 4 Drawing Sheets

(51) Int. Cl.
  *C01B 3/06* (2006.01)
  *C01B 3/00* (2006.01)
  *C07C 211/63* (2006.01)
(52) U.S. Cl.
  CPC ........ *C07D 295/037* (2013.01); *C07F 9/5407* (2013.01); *C07C 2601/14* (2017.05); *Y02E 60/324* (2013.01); *Y02E 60/362* (2013.01)
(58) Field of Classification Search
  CPC ............... C07C 211/63; C07C 2101/14; Y02E 60/324; Y02E 60/362
  See application file for complete search history.

(56) References Cited

U.S. PATENT DOCUMENTS

| | | | |
|---|---|---|---|
| 2003/0094380 A1* | 5/2003 | Moulton | B01D 61/44 205/431 |
| 2006/0222584 A1 | 10/2006 | Welz-Biermann et al. | |
| 2007/0097598 A1 | 5/2007 | Siggel et al. | |
| 2008/0251759 A1 | 10/2008 | Kalb et al. | |
| 2010/0015040 A1 | 1/2010 | Kim et al. | |
| 2011/0100356 A1 | 5/2011 | Bliesner | |

FOREIGN PATENT DOCUMENTS

| | | |
|---|---|---|
| EP | 1 640 654 | 3/2006 |
| EP | 1 726 593 | 11/2006 |
| FR | 2870534 | 11/2009 |
| JP | 2010013290 | 1/2010 |
| WO | WO 2004035464 | 4/2004 |
| WO | WO 2005/021484 | 3/2005 |
| WO | WO 2008/052860 | 5/2008 |
| WO | WO 2008/052863 | 5/2008 |
| WO | WO 2009/101201 | 8/2009 |
| WO | WO 2010/081657 | 7/2010 |
| WO | WO2010081657 | * 7/2010 |
| WO | WO 2011/139708 | 11/2011 |

OTHER PUBLICATIONS

Cakanyildirim, Cetin; Guru, Metin; "Hydrogen cycle with sodium borohydride", International Journal of Hydrogen Energy (2008), vol. 33, Issue 17, pp. 4634-4639.
Cakanyildirim, Cetin; Guerue, Metin; "Processing of NabH$_4$ from NaBO$_2$ with MgH$_2$ by ball milling and usage as hydrogen carrier", Renewable Energy (2010), vol. 35, Issue 9, pp. 1895-1899.
Demirci, U. B.; Akdim, 0.; Miele, P.; "Ten-year efforts and a no-go recommendation for sodium borohydride for on-board automotive hydrogen storage", International Journal of Hydrogen Energy (2009), vol. 34, Issue 6, pp. 2638-2645.
Park, Eun Hee; Jeong, Seong UK; Jung, Un Ho; Kim, Sung Hyun; Lee, Jaeyoung; Nam, Suk Woo; Lim, Tae Hoon; Park, Young Jun; Yu, Yong Ho; "Recycling of sodium metaborate to borax" International Journal of Hydrogen Energy (2007), vol. 32, Issue 14, pp. 2982-2987.
Kojima, Yoshitsugu.; Chuo Kenkyusho; "Hydrogen Storage and Generation Using Sodium Borohydride", R&D Review of Toyota CRDL (2005), vol. 40, No. 2, pp. 31-36.
Kojima, Yoshitsugu; Haga, Tetsuya; "Recycling process of sodium metaborate to sodium borohydride", International Journal of Hydrogen Energy (2003), vol. 28, Issue 9, pp. 989-993.
Li, Z. P.; Liu, B. H.; Zhu, J. K.; Morigasaki, N.; Suda, S.; "NaBH4 formation mechanism by reaction of sodium borate with Mg and H2", Journal of Alloys and Compounds (2007), vol. 437, Issues 1-2, pp. 311-316.
Liu, Bin Hong; Li, Zhou Peng; Zhu, Jing Ke; Morigasaki, N.; Suda, S.; "Alkali Oxide Addition Effects on Borohydride Formation during the Reaction of Al, Si, and Ti with Borate and Hydrogen", Energy & Fuels, 2008 American Chemical Society, pp. 1894-1896.
Morigasaki, Nobuto; Tanisawa, Kazuhiro; Li, Zhoupeng; Suda, Seijirau; Kogakuin Daigaku Kenkyu Hokoku (2002), 93 55-59.
Ong, et al. "Investigation of the Effect of Functional Group Substitutions on the Gas-Phase Electron Affinities and Ionization Energies of Room-Temperature Ion Liquids Ions using Density Functional Theory", Electrochimica Acta, Elsevier Science Publishers, Barking, GB, vol. 55, No. 11, Apr. 15, 2010, p. 3804-3811, XP026978449.
Saitoh, Yasuo; Yoshizaki, Atsuhiro; Ibaraki Kogyo Koto Senmon Gakko Kenkyu Iho (2009), 44, 47-54.
Suda, S.; Morigasaki, N.; (wase, Y.; Li, Z. P.; "Production of sodium borohydride by using dynamic behaviors of protide at the extreme surface of magnesium particles" Journal of Alloys and Compounds (2005), vols. 404-406, pp. 643-647.
Wasserscheid, Peter; Welton, Tom (Eds.); "Ionic Liquids in Synthesis, Second Edition", Wiley-VCH 2008; ISBN 978-3-527-31239-9.
Zhang et al., Interactions between macromolecules and ions: The Hofmeister series; Current Opinion in Chemical Biology 2007,10 (6):658-663.
International Preliminary Report on Patentability for PCT Application Serial No. PCT/EP2012/076305 dated Aug. 5, 2014 (10 pgs).
Bürchner et al., "Synthesis and Characterization of Boranate Ionic Liquids (BILs)", Chem. Eur. J. 2012, 18, pp. 2254-2262.

* cited by examiner

USE OF AN IONIC LIQUID FOR STORING HYDROGEN

The present invention relates to ionic liquids which are particularly useful for storing and releasing hydrogen, e.g. in a borohydride/borate system.

Ionic liquids for storing and releasing hydrogen in a borohydride/borate system are e.g. disclosed in WO 2010/081657.

According to generally accepted literature an ionic liquid is a salt in the liquid state, more particularly a melt of a low melting salt, e.g. with a melting point equal or below 100° C. (see e.g. Wasserscheid, Peter; Welton, Tom (Eds.); "Ionic Liquids in Synthesis", Wiley-VCH 2008; ISBN 978-3-527-31239-9). However, it is to note that the melting temperature of ≤100° C. is chosen arbitrarily.

Such ionic liquids may exhibit some very interesting characteristics, e.g. having a very low, virtually non measurable, vapor pressure, a large liquidus range, good electrical conductivity and interesting solvation characteristics. These characteristics make ionic liquids prone for several applications, e.g. as solvents (for example, in organic or inorganic synthesis, transition metal catalysis, biocatalysis, multiphase reactions, photochemistry, polymer synthesis, and nanotechnology), extracting agent (e.g. liquid-liquid or liquid gaseous extraction, sulphur removal during crude oil processing, removal of heavy metals during water processing and liquid membrane extraction), electrolytes (for example, in batteries, fuel cells, capacitors, solar cells, sensors, electroplating, electrochemical metal processing, electrochemical synthesis, and nanotechnology), lubricants, thermofluids, gels, reagents for organic synthesis, in the so-called "green chemistry" (e.g. as replacement for volatile organic compounds), antistatic additives, specific applications in chemical analysis (e.g. gas chromatography, mass spectroscopy, capillary zone electrophoresis), liquid crystals, etc. and particularly for storing and releasing hydrogen.

When investigating the storing and releasing of hydrogen in ionic liquid based on borohydrides, a decrease of the molar mass of the cation may increase the hydrogen storage density. A preferred molecular weight of the cation used according to the present invention includes about 70 g/mol, e.g. 72 g/mol, 74 g/mol up to 185 g/mol, preferably 125 g/mol and less, more preferably 105 g/mol and less.

Low melting points and low viscosity are of crucial importance to operate borohydride ionic liquids as hydrogen storage media according to the present invention: The liquid hydrogen storage has to be pumpable even at low temperatures for e.g. automotive applications; the viscosity of the liquid directly affects reachable reaction speeds in the total process, e.g. at the catalysator system to release a required volume flow of hydrogen or at the recycling system to get a quick and quantitative phase separation.

To achieve low melting point and viscosity it is possible to e.g. increase the length of the side chains of the quaternary ammonium or phosphonium cation or to add suiteable diluents. Both strategies are contradictory in order to keep the hydrogen storage capacity as high as possible.

It has been found that, when using quaternary ammonium or phosphonium borohydrides as ionic liquids, their melting points and viscosities are increasing with lowering molecular weight of the cation to increase the hydrogen storage density. Especially if one decreases the molar weight of the cation near to M=100 g/mol or lower (e.g. near to that of the tetramethylammonium cation) the melting points reach values far above room temperature. Also there is a correlation of the melting point and size-branching degree of tetralkylammonium tetrahydroborates, namely, the melting point decreases with enhanced branching degree; see e.g. FIG. 4.

It order to get such quaternary ammonium or phosphonium borohydride liquid at room temperature or even below, a diluent must be used. Because of obvious advantages water is an ideal diluent for ammonium and phosphonium borohydrides, moreover low molecular weight borohydrides demonstrate excellent solubility in water.

However, there are two problems connected therewith: Firstly, such aqueous formulations may have stability problems at elevated temperatures. Secondly, the apparent advantage of a homogenous system turns into a drawback after release of the hydrogen, e.g. in the recycling phase. In fact, formed low molecular weight quaternary ammonium or phosphonium borate remains in homogenous aqueous solution after addition of an inorganic borohydride, meaning that no ion exchange occurs, whereas, in the recycling phase, the use of high molecular weight borohydrides results in spontaneous phase separation between organic borohydride and aqueous phase of inorganic borate, as e.g. described in WO 2010/081657.

According to the present invention, surprisingly a process has been found to overcome such drawbacks: Namely a recycling process with an easy workup method for separating the recycled hydrogen storing borohydride ionic liquid from byproducts and provide this ionic liquid in a stable, homogenous solution in water.

In one aspect the present invention provides a method of storing hydrogen by treating a second ionic liquid which comprises a cation and an anion comprising borate with borohydride, to obtain a first ionic liquid comprising releasable hydrogen characterized in that
  (i) the first and the second ionic liquid both are water miscible,
  (ii) the first ionic liquid is separated, particularly is salted out, from solution in water by adding a phase separation inducer, and
  (iii) the second ionic liquid is obtained by releasing the hydrogen out of the first ionic liquid under use of water optionally in the presence a catalyst; and optionally
  (iv) the first ionic liquid further comprises inorganic borohydride, in particular $NaBH_4$, $KBH_4$, $LiBH_4$, to an extent that the first ionic liquid remains water miscible and the second ionic liquid after the release of hydrogen remains water miscible.

A method provided by the present invention is herein also designated as "a method of (according to) the present invention.

A first ionic liquid in a method according to the present invention is an organic borohydride comprising the cation of the second ionic liquid and a borohydride as an anion. Such first ionic liquid may be provided by treating a starting salt comprising a cation as present in the first and second ionic liquid, e.g. as described below, see e.g. the group of formula $(CH_3)_3((CH_3)_2-CH))N^+$ in FIG. 1, and an appropriate starting anion, e.g. selected from halogen, e.g. Cl, Br, I, a carbonate of formula $RCO_3^-$, a phosphate of formula $R_2PO_3^-$, a sulfate ($SO_4^{2-}$), e.g. of formula $RSO_4^-$, wherein R is C1 to C6 alkyl, e.g. C1 to C4 alkyl, see. e.g. "Y−" in FIG. 1, with an inorganic borohydride, e.g. in particular $NaBH_4$, $KBH_4$ and/or $LiBH_4$, see e.g. FIG. 1 (101). The cation and the starting anion are chosen such that a homogene aqueous solution of the salt may be obtained. To the solution obtained a phase separation inducer, e,g, such as described below, is added, see e.g. "A⁺B−", FIG. 1 (102) and (103), whereupon a water containing mixture of a first ionic liquid is obtained, see e.g. the compound $(CH_3)_3((CH_3)_2-$ CH))N—BH$_4$ in FIG. 1, and a salt comprising the cation from the inorganic borohydride and the starting anion from the starting salt, optionally and preferably in combination with phase separation inducer "A$^+$B$^-$", separates out as an aqueous solution (see e.g. FIG. 1 (104)), and can be isolated e.g. by phase separation, e.g. including centrifugation.

Such process is novel and also forms part of the present invention.

In a further aspect the present invention provides a process for the preparation of an ionic liquid comprising releasable hydrogen, characterized in, that
 (a) an aqueous solution of a starting salt comprising the cation of said ionic liquid and a starting anion selected from halogen, e.g. Cl, Br, I, a carbonate of formula RCO$_3^-$, a phosphate of formula R$_2$PO$_3^-$, a sulfate (SO$_4^{2-}$), in particular of formula RSO$_4^-$, wherein R is C1 to C6 alkyl, is reacted with an inorganic borohydride, such as NaBH$_4$, KBH$_4$ and/or LiBH$_4$, to obtain a homogeneous aqueous solution,
 (b) treating the homogeneous aqueous solution of step (a) with a phase separation inducer whereupon a salt comprising the cation from the inorganic borohydride and the starting anion from the starting salt used, optionally in combination with the phase separation inducer separates from the water containing ionic liquid, and
 (c) separating the phases formed in (b) and isolating the first ionic water containing liquid from the phase which comprises the salt obtained in (b).

The second ionic liquid according to the present invention is obtained from the first ionic liquid by releasing the hydrogen, e.g. by use of water, optionally in combination with a catalyst, e.g. as described below, see e.g. FIG. 1 (105), to obtain a salt comprising the cation of said ionic liquids and a borate in aqueous solution, see e.g. the compound (CH$_3$)$_3$((CH$_3$)$_2$—CH))N—BO$_2$. That borate salt may be reacted with an inorganic borohydride, such as NaBH$_4$, KBH$_4$ and/or LiBH$_4$, in aqueous solvent, see e.g. (106) in FIG. 1, to obtain a first ionic liquid comprising releasable hydrogen and a borate salt, e.g. a sodium, potassium, lithium, magnesium or calcium salt corresponding to the inorganic borohydride used in aqueous solution. For separating the first ionic liquid from the borate salt, a phase separation inducer, such as described below, see e.g. "A$^+$ B$^-$", FIG. 1 (107), is used. Two phases are formed. One phase comprises the first water containing ionic liquid and the second phase comprises the borate salt, e.g. beside the separation inducer. The phases are separated, e.g. including centrifugation and the borate salt and the first ionic liquid are isolated, see e.g. FIG. 1 (108), and may be converted into an inorganic borohydride, e.g. K, Li, Na, see e.g. FIG. 1 (109) for use in the preparation of a first ionic liquid, see e.g. FIG. 1 (106).

The preparation of the first and second ionic liquid and the whole reaction cycle is schematically shown in FIG. 1.

A method provided by the present invention is herein also designated as "a method of (according to) the present invention.

An ionic liquid in a method of the present invention is regarded to be water miscible if a saturated aqueous solution of said ionic liquid at room temperature is formed with 50% by weight of water or less, preferably 40% by weight or less, such as 20% by weight or less, e.g. 10% or less, e.g. (ca.) 5% to 50% by weight.

The term "ionic liquid" as used herein, e.g. in a process of the present invention, includes salts with melting temperatures of up to 250° C., e.g. ≤100° C. and >100° C., but ≤250° C.; preferably ≤100° C. and more preferably less than room temperature.

The term "ionic liquid" as used herein, e.g. in a process of the present invention, further includes all liquid organic salts and mixtures of salts consisting of organic cations, organic anions or inorganic anions. Moreover additional salts with inorganic cation and organic or inorganic anion can be dissolved in the ionic liquid, containing but definitely not limited to the identical anion or identical anions as found in the basic ionic liquid. Moreover additives may be dissolved in the ionic liquid.

In a process of the present invention the cation is a quaternary or protonated cation, preferably a quaternary cation. According to an exemplary embodiment in a method of the present invention the cation comprises one to four moieties out of the group consisting of hydrogen, C1-C8-alkyl, C2-C8-alkenyl, C2-C8-alkinyl, C3-C8-cycloalkyl, C3-C8-cycloalkenyl, C5-C6-aryl, and C5-C6-heteroaryl, more preferably the one to four moieties may be selected out of the group consisting of hydrogen, C1-C8-alkyl, C2-C4-alkenyl, C2-C4-alkinyl, C3-C6-cycloalkyl, C3-C4-cycloalkenyl, such as C1-C8-alkyl, C3-C6-cycloalkyl.

In general, branched alkyl, alkenyl and alkinyl chains and/or cyclic structures including heterocyclic cations are superior over linear chains.

For clarity reasons it should be mentioned that in this application the term C1-C20-alkyl or similar terms is an abbreviatory notation for C1-alkyl, C2-alkyl, . . . , up to C20-alkyl or similar terms.

According to an exemplary embodiment of the method of the present invention the cation is one out of the group consisting of pyridinium, pyrrolium, ammonium, phosphonium, piperidinium, pyrrolidinium, morpholinium, imidazolium, pyrazolium.

According to another exemplary embodiment of the method of the present invention the cation is preferably one out of the group of ammonium, pyrrolidinium, morpholinium, piperidinium; or pyridinium, pyrrolium, imidazolium, pyrazolium, or phosphonium.

According to an exemplary embodiment of the method of the present invention the cation is one out of the group consisting of pyridinium, pyrrolium, wherein one moiety is bound to the nitrogen atom and/or one to three moieties are bound to carbon atoms of the carbon ring.

According to an exemplary embodiment of the method of the present invention the cation is one out of the group consisting of ammonium and phosphonium, e.g. ammonium, e.g. phosphonium.

According to an exemplary embodiment of the method of the present invention the cation is one out of the group consisting of piperidinium, pyrrolidinium and morpholinium, wherein one or two of the one to four moieties is bound to the nitrogen atom and/or one to three of the one to four moieties are bound to carbon atoms of the carbon ring.

In another aspect of the method of the present invention the cation is pyridinium.

In another aspect of the method of the present invention the cation is pyrrolium.

In another aspect of the method of the present invention the cation is ammonium.

In another aspect of the method of the present invention the cation is phosphonium.

In another aspect of the method of the present invention the cation is piperidinium.

In another aspect of the method of the present invention the cation is pyrrolidinium.

In another aspect of the method of the present invention the cation is morpholinium.

In another aspect of the method of the present invention the cation is imidazolium.

In another aspect of the method of the present invention the cation is pyrazolium.

According to an exemplary embodiment of the method of the present invention the cation is one out of the group consisting of imidazolium and pyrazolium, wherein a respective one of the one to four moieties is bound to each nitrogen atom and/or one to three of the one to four moieties are bound to carbon atoms of the carbon ring. For clarity reasons it should be noted that in case of more than one nitrogen 7 atom a first moiety may be bound to a first nitrogen atom and a second moiety may be bound to a second nitrogen atom.

According to an exemplary embodiment of the method the cation is one out of the group consisting of tetramethylammonium, tetraethylammonium, triethylmethylammonium, tetrabutylammonium, tributylmethylammonium, 1,3-dimethylimidazolium, 1-butyl-3-methylimidazolium, trimethyl-iso-propylammonium, 1,2,3-trimethylimidazolium, 1-ethyl-3-methylimidazolium, 1-ethyl-2,3-dimethylimidazolium, and 1-butyl-2,3-dimethylimidazolium, particularly trimethyl-iso-propylammonium, which may all be used together with $BH_4^-$ as an anion.

According to another exemplary embodiment of the method of the present invention the cation is preferably one out of the group of N-butyl-N-methylpyrrolidinium, N-propyl-N-methylpyrrolidinium, N-ethyl-N-methylpyrrolidinium, N,N-dimethylpyrrolidinium, N-tert.butyl-N-methylpyrrolidinium, N-iso-propyl-N-methylpyrrolidinium, N-iso-propyl-N-ethylpyrrolidinium, N,N-di-iso-propylpyrrolidinium, N-tert.butyl-N-ethylpyrrolidinium, N,N-di-tert.butylpyrrolidinium, N-tert.butyl-N-iso-propylpyrrolidinium, N-butyl-N-methylmorpholinium, N-propyl-N-methylmorpholinium, N-ethyl-N-methylmorpholinium, N,N-dimethylmorpholinium, N-tert.butyl-N-methylmorpholinium, N-iso-propyl-N-methylmorpholinium, N-iso-propyl-N-ethylmorpholinium, N,N-Di-iso-propylmorpholinium, N-tert.butyl-N-ethylmorpholinium, N,N-di-tert.butylmorpholinium, N-tert.butyl-N-iso-propylmorpholinium, N-butyl-N-methylpiperidinium, N-propyl-N-methylpiperidinium, N-ethyl-N-methylpiperidinium, N,N-dimethylpiperidinium, N-tert.butyl-N-methylpiperidinium, N-iso-propyl-N-methylpiperidinium, N-iso-propyl-N-ethylpiperidinium, N,N-di-iso-propylpiperidinium, N-tert.butyl-N-ethylpiperidinium, N,N-di-tert.butylpiperidinium, N-tert.butyl-N-iso-propylpiperidinium, trimethyl-iso-propylammonium, dimethyl-di-iso-propylammonium, methyl-tri-iso-propylammonium, tetra-iso-propylammonium, trimethyl-tert.-butylammonium, dimethyl-di-tert.-butylammonium, methyl-tri-tert.-butylammonium, tetra-tert.-butylammonium, trimethyl-iso-propylphosphonium, dimethyl-di-iso-propylphosphonium, methyl-tri-iso-propylphosphonium, tetra-iso-propylphosphonium, trimethyl-tert.-butylphosphonium, dimethyl-di-tert.-butylphosphonium, methyl-tri-tert.-butylphosphonium, tetra-tert.-butylphosphonium, which may all be used together with $BH_4^-$ as an anion.

According to another exemplary embodiment of the method of the present invention the cation is preferably one out of the group of N-propyl-N-methylpyrrolidinium, N-ethyl-N-methylpyrrolidinium, N,N-dimethylpyrrolidinium, N-tert.butyl-N-methylpyrrolidinium, N-iso-propyl-N-methylpyrrolidinium, N-butyl-N-methylmorpholinium, N-propyl-N-methylmorpholinium, N-ethyl-N-methylmorpholinium, N,N-dimethylmorpholinium, N-tert.butyl-N-methylmorpholinium, N-iso-propyl-N-methylmorpholinium, N-butyl-N-methylpiperidinium, N-propyl-N-methylpiperidinium, N-ethyl-N-methylpiperidinium, N,N-dimethylpiperidinium, N-tert.butyl-N-methylpiperidinium, N-iso-propyl-N-methylpiperidinium, trimethyl-iso-propylammonium, dimethyl-di-iso-propylammonium, trimethyl-tert.-butylammonium, dimethyl-di-tert.-butylammonium, trimethyl-iso-propylphosphonium, dimethyl-di-iso-propylphosphonium, trimethyl-tert.-butylphosphonium, dimethyl-di-tert.-butylphosphonium, which may all be used together with $BH_4^-$ as an anion.

According to an exemplary embodiment of the method of the present invention the cation is preferably one out of the group of 1-methyl-1-iso-butyl-piperidinium, trimethyl-iso-propylammonium, dimethyl-n-butyl-(2-ethyl-n-hexyl)-ammonium, methyl-diisopentyl-(2-methyl-5-dimethyl-n-hexyl)-ammonium, methyl-tri(2-ethyl-n-hexyl)-ammonium, N-methyl-N-n-butyl-pyrrolidinium, N-methyl-N-iso-butyl-pyrrolidinium, N-methyl-N-octyl-pyrrolidinium, N-methyl-N-(2-ethyl-n-hexyl)-pyrrolidinium, cyclohexyl-dimethyl-(2-ethyl-n-hexyl)-ammonium, N-methyl-N-ethyl-morpholinium, N,N-dimethyl-pyrrolidinium, trimethyl-isopropyl-ammonium, N-dimethyl-morpholinium, tetraethylammonium, tetramethylammonium, which may all be used together with $BH_4^-$ as an anion.

According to another exemplary embodiment of the method of the present invention the cation is preferably one out of the group of ammonium, pyrrolidinium, morpholinium, piperidinium, such as tetramethylammonium, tetraethylammonium, trimethyl-iso-propylammonium, dimethyl-n-butyl-2-ethyl-n-hexylammonium, di(iso-pentyl)-5-dimethyl-3-methyl-n-hexyl-methylammonium, tri-(2-ethyl-n-hexyl)-methylammonium, dimethyl-cyclohexyl-2-ethyl-n-hexyl-ammonium, 1,1-dimethyl-pyrrolidinium, 1-methyl-1-n-butyl-pyrrolidinium, 1-methyl-1-iso-butyl-pyrrolidinium, 1-methyl-1-octyl-pyrrolidinium, 1-methyl-1-(2-ethyl-n-hexyl)-pyrrolidinium, 1-methyl-1-ethylmorpholinium, 1,1-dimethyl-morpholinium, 1-methyl-1-iso-butylpiperidinium, which may all be used together with $BH_4^-$ as an anion.

According to an exemplary aspect of the present invention an ionic liquid for storing hydrogen is provided, wherein the ionic liquid comprises a cation and an anion comprising borate, in particular metaborate. The borate may comprise or may consist of B, O and in some cases H-Atoms and may be formed by metaborate or polyborate. In particular, the borate or metaborate may be part of or may form the anion of the ionic liquid. The cation may comprise or may consist of quaternary material, e.g. trimethyl-iso-propylammonium.

Furthermore, the ionic liquid (mixture) may have a predetermined viscosity value, e.g. in water. In particular, the viscosity value may be set, e.g. according to a desired level. According to an exemplary embodiment in a method of the present invention by releasing hydrogen a borate, e.g. metaborate or any compound corresponding to the generic formula BOR' or BOR'R", is formed, wherein R' and R" is as defined above. In particular, the metaborate may form the anion of an ionic liquid.

In a process of the present invention preferably the term "borohydride" is used in the broadest possible way, i.e. may particularly denote any molecule, compound, radical or complex which comprises boron and at least one hydrogen atom. That is, every compound which can be written by the generic formula BHR'R"R'" or $BH_3X^-$ or $B_2H_6X^-$, where $X^-$ is any anion forming complexes with borane or diborane, may be denoted as borohydride. For example, R', R", R'"

may be hydrogen atoms, or a hydrocarbon of 1 to 10 C-atoms, including e.g. alkyl, alkenyl, alkinyl, cycloalkyl, cycloalkenyl, aryl or heteroaryl, wherein each rest R may be independently substituted by one of the moiety stated above. The cation in a borohydride suitable in a process of the present invention, e.g. for preparing the first ionic liquid, e.g. according to FIG. 1 (101), or recyclization according to FIG. 1 (106), or for use as a separation inducer, includes any appropriate cation, e.g. alkali borohydrides, such as $NaBH_4$, $KBH_4$, $LiBH_4$. Preferably the borohydride, e.g. used for preparing the first ionic liquid, recyclization or used as a separation inducer is sodium borohydride ($NaBH_4$).

By providing a borohydride ionic liquid according to the present invention, e.g. the first ionic liquid, an ionic liquid for storing hydrogen and a method of storing hydrogen is provided which may be efficient and/or may provide a secure method of operation. In particular, the borohydride may form together with the cation an ionic liquid enabling an easy and secure handling which may be used as an energy source or energy carrier for cars, for example. In particular, the handling may be similar to common gasoline, since the ionic liquid may also be a liquid as common gasoline. Thus, no pressurized hydrogen or additional carriers like metal hydrides may be necessary, which may only be formed under specific conditions. Therefore, the use of ionic liquids may be more secure since no specific conditions may be necessary or at least the restrictions concerning specific conditions, e.g. temperature range, may be lessened. It should be noted that the viscosity of the ionic liquid may be decreased by adequate provisions, e.g. by increasing the temperature. The use of such ionic liquids for hydrogen storage may also provide a storing medium which may induce low corrosion in containers or the like used to store the ionic liquid. Thus, it may be possible to omit a corrosion inhibitor.

A suitable phase separation inducer $A^+B$ in a method according to the present invention includes any organic or inorganic salt which strongly coordinates to water and does not react with borohydride, borate or any other compound involved as described above. Such phase separation inducer is also designated herein as "coordinating (organic or inorganic) salt". By forming hydrogen bonds with the water, $A^+B^-$ withdraws solvation power of the water from the reaction systems to induce an ion exchange process followed by phase separation (salting out), whereupon the more hydrophobic borohydride anion combines with the more hydrophobic quaternary or protonated organic cation and the more hydrophilic anion $Y^-$ or any form of borate combines with the more hydrophilic cation, being the counterion of the induced borohydride, see (101) or (106) in FIG. 1 as examples.

$A^+B^-$ includes any salt, that shows a high solubility in water, e.g. 25 g in 100 g water at 20° C. and more and/or is hygroscopic.

In one aspect a suitable phase separation inducer $A^+B$ in a method according to the present invention include salts like NaCl, $Na_2SO_4$, NaOH, $Na_2CO_3$, $NaCH_3CO_2$, $NaH_2PO_4$, $Na_2HPO_4$, KCl, $K_2SO_4$, KOH, $K_2CO_3$, $KCH_3CO_2$, $KH_2PO_4$, $K_2HPO_4$, LiCl, $LiCH_3CO_2$, $Mg(CH_3CO_2)_2$, $MgSO_4$, $CaCl_2$, $Ca(CH_3CO_2)_2$, $NH_4Cl$, $(NH_4)_2SO_4$, $NH_4CH_3CO_2$.

The effect of inducing phase separation by reducing solvation power of water is known in the case of proteins, see e.g. "Interactions between macromolecules and ions: The Hofmeister series; Current Opinion in Chemical Biology 2006, 10:658-663; Yanjie Zhang and Paul S Cremer". The salts with high power to precipitate proteins described in the Hofmeister Series—but not limited to, are considered to be possibly suitable as phase separation inducer in a method of the present invention. In another aspect a suitable phase separation inducer $A^+B$ in a method according to the present invention include salts with high power to precipitate proteins.

During investigating the present invention surprisingly it turned out, that three types of salts are particularly suitable and especially preferred:

1.) The borates, e.g. as exemplified in FIG. 1 (108): In that case $A^+B^-$ and the borate, e.g. inorganic borate, namely $NaBO_2$ are identical. If a borohydride other than sodium borohydride is used, a corresponding borate will result, e.g. $KBO_2$, $LiBO_2$.
2.) The induced borohydrid itself, e.g. $NaBH_4KBH_4$, $LiBH_4$, such as $NaBH_4$ as exemplified in FIG. 1 (101) or (106): In that case this borohydride is an excess to the needed borhydride based on the 1:1 stoichometry.
3.) Any additive being part of the formulation, e.g. a stabilizing additive, preferably out of the group of basic salts like alkaline metal hydroxides, alkaline metal carbonates, tetraalkylammonium hydroxides, tetraalkylammonium carbonates, tetraalkylphosphonium hydroxides, tetraalkylphosphonium carbonates, and any kind of alkylcarbonates, especially with identical cation to the cation chosen for the ionic liquid hydrogen storage system.

In another aspect a suitable phase separation inducer $A^+B$ in a method according to the present invention includes borates, borohydrides and stabilizing additives.

In one particular embodiment of the present invention the phase separation inducer is a hydroxide, carbonate, alkylcarbonate, borohydride and/or metaborate, e.g. a borate anion of the second ionic liquid.

In the above described three cases, the phase separation inducer $A^+B^-$ is a chemical being already part of the chemistry itself or a part of the formulation and therefore no new substance has to be induced and possibly separated.

According to an exemplary embodiment of the method of the present invention the first ionic liquid and/or the second ionic liquid each has a predetermined viscosity value. In particular, the first ionic liquid and the second ionic liquid may have the same viscosity or different viscosity. For example, a first predetermined viscosity value may be associated with the first ionic liquid, while a second predetermined viscosity level may be associated with the second ionic liquid. In particular, the viscosity value may be set, e.g. according to a desired level, e.g. below 100 mPas at room temperature and/or below 2000 mPas at −20° C.

According to an exemplary embodiment in a method of the present invention the viscosity level is set to the predetermined viscosity value by adding an additive. In particular, the additive may be adapted to decrease the viscosity, e.g. may be an agent having a lower viscosity than the ionic liquid, i.e. the hydrogen storing liquid. Furthermore, the additive may not react with the ionic liquid and/or a used catalyst. Thus, in general no esters, aldehydes, ketones, carbonic acids may be used beside ones which are sterically inhibited, i.e. aldehydes, ketones or carbonic acids which does not react with the ionic liquid and/or catalyst due to sterically inhibiting may be used for example.

In general, additives may be protective additives, e.g. for protection for corrosion, wear, high pressure, oxidation and/or reduction processes, buffering substances, e.g. for pH level buffering and/or acid capturing agents, complexing agents, emulgators, dispersion mediums, detergents, lubricants, friction modification agents, viscosity modification agents, gelling agents, sealing agents, preservative agents, so-called pour-point additives, foam inhibitors, radical interceptors, and water regulating agents.

In particular, an additive may be used having a low vapor pressure, high boiling point and a low freezing point. Additionally, an additive may be used which can be readily removed out of hydrogen gas, e.g. as a gas phase. The removing may be effected by an adsorbent, e.g. activated charcoal. Furthermore, the used additive may not be solvable in or mixable with water so that it may not be removed during a recycling process.

According to an exemplary embodiment the additive is one out of the group consisting of amide, ether, including cyclic or polyether, acetals, ketals, alcohols, including polyalcohols, aromatic hydrocarbons, aliphatic hydrocarbons, e.g. butanols, pentanols, hexanols, heptanols, octanols, fatty alcohols, dibutylethers, diethylethers, methyl tert-butyl ethers, ethyl tert-butylethers, 1,2-diethoxyethanes, formaldehyde dimethylacetales, polyethylene glycol dimethylethers of different chain lengths, and polyvinyl alcohols of different chain lengths, water.

According to an exemplary embodiment the method further comprises adding a basic additive to the first ionic liquid and/or the second ionic liquid. That is, an additive may be used having a pH-value of more than 7. In particular, the basic additive may have a stabilizing effect and may also be called stabilizer.

According to an exemplary embodiment of the method the basic, e.g. stabilizing additive is at least one out of the group consisting of alkaline metal hydroxides, alkaline earth metal hydroxides, alkaline metal carbonates, alkaline earth metal carbonates, quaternary tetraalkylammonium hydroxides, quaternary tetraalkylammonium carbonates, quaternary tetraalkylphosphonium hydroxides, quaternary tetraalkylphosphonium carbonates, and alkylcarbonates. In particular, a mixture of more than one of the mentioned basic additives may be used.

Summarizing, according to an exemplary aspect of the present invention a process for storing hydrogen may be provided. The process may form a closed loop and may be based on liquid carrier materials, like ionic liquids. In particular, the liquid carrier may comprise cations, e.g. trimethyl-iso-propylammonium, and anions which may be formed by borohydride and which may carry the stored hydrogen. The cations and anions may form an ionic liquid which may stable even when in contact with water. However, the stored hydrogen may be released by using water and a respective catalyst, e.g. a transition metal or noble metal like platinum, palladium or rhodium. Under these circumstances the ionic liquid may release the hydrogen while a new ionic liquid may be formed comprising trimethyl-iso-propylammonium and a borate, e.g. metaborate. This new ionic liquid may then be loaded with hydrogen again, e.g. by introducing sodium borohydride into the ionic liquid.

The method of storing hydrogen by using an ionic liquid according to the present invention may provide an efficient and secure way of storing hydrogen. In particular, it may be possible to store a sufficient amount without using high pressure or low temperatures. For example, the use of ionic liquids comprising trimethyl-iso-propylammonium as a cation and metaborate or borohydride as anions may enable the provision of liquid storage media wherein the ionic liquid may be loaded and unloaded with hydrogen in a cycle or recycling process, e.g. by using a liquid ion exchange process. This ionic liquid may provide a sufficiently high storage density of the hydrogen which may be released in a controllable manner by using a catalyst. In general it may be possible to provide a storage medium ensuring a sufficient range for a car, for example. By using an ionic liquid as storage media it may be possible to ensure a high storage capacity per mass and/or a high storage capacity per volume. Additionally, low leakage possibly leading to a high storage security may be achievable. Furthermore, the described ionic liquids may have a high stability over time with respect to chemical and/or thermal influences and/or may be flame resistant.

In another aspect the present invention provides a ionic liquid comprising a cation selected from 1-methyl-1-iso-butyl-piperidinium, trimethyl-iso-propylammonium, dimethyl-n-butyl-(2-ethyl-n-hexyl)-ammonium, methyl-diisopentyl-(2-methyl-5-dimethyl-n-hexyl)-ammonium, methyl-tri(2-ethyl-n-hexyl)-ammonium, N-methyl-N-n-butyl-pyrrolidinium, N-methyl-N-iso-butyl-pyrrolidinium, N-methyl-N-octyl-pyrrolidinium, N-methyl-N-(2-ethyl-n-hexyl)-pyrrolidinium, cyclohexyl-dimethyl-(2-ethyl-n-hexyl)-ammonium, N-methyl-N-ethyl-morpholinium, N,N-dimethyl-pyrrolidinium, trimethyl-isopropyl-ammonium, N-dimethyl-morpholinium, tetraethylammonium, tetramethylammonium and a borohydride, e.g. for storing hydrogen, or a borate, in particular metaborate, e.g. useful for preparing a ionic liquid for storing hydrogen.

It has been found that the addition of inorganic borohydride, such as $NaBH_4$, $KBH_4$ and/or $LiBH_4$ to a first ionic liquid as provided by the present invention, e.g. in an amount such that the first ionic liquid remains water miscible after such addition and the second ionic liquid remains water miscible after the release of hydrogen in the presence of the additional borate created, may increase the hydrogen storage capacity of the first ionic liquid.

In another aspect the present invention provides an ionic liquid a for storing, e.g. and releasing hydrogen, the ionic liquid comprising a cation as described above and further comprising an inorganic borohydride, such as $NaBH_4$, $KBH_4$, and/or $LiBH_4$, and A method of storing hydrogen by treating a second ionic liquid which comprises a cation and an anion comprising borate with borohydride, to obtain a first ionic liquid comprising releasable hydrogen, characterized by (i), (ii), (iii) as described above and further characterized in that (iv) the first ionic liquid further comprises inorganic borohydride, such as $NaBH_4$, $KBH_4$, and/or $LiBH_4$, to an extent, that the first ionic liquid remains water miscible and the second ionic liquid after the release of hydrogen remains water miscible.

It is believed that the presence of the organic borohydride resulting from the treatment of an ionic liquid with borohydride may stabilize a first organic liquid comprising inorganic borohydride and thus the hydrogen storage capacity may be enhanced.

Other possible cations may include tetramethylammonium, tetraethylammonium, triethylmethylammonium, tetrabutylammonium, tributylmethylammonium, 1,3-dimethylimidazolium, 1-butyl-3-methylimidazolium, 1,2,3-trimethylimidazolium, 1-ethyl-3-methylimidazolium, 1-ethyl-2,3-dimethylimidazolium, and 1-butyl-2,3-dimethylimidazolium which may all be used together with $BH_4$ as an anion.

Figure 1:
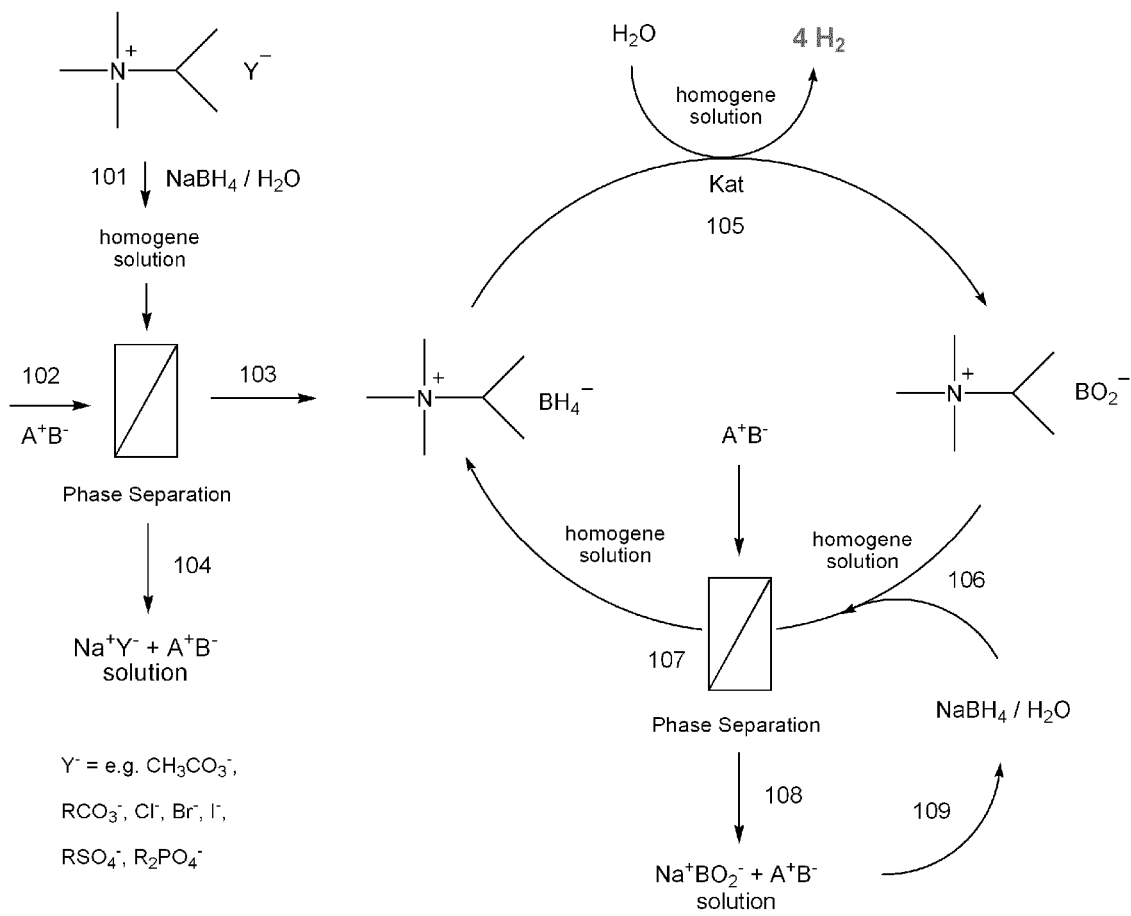
FIG. 1 schematically illustrates a cycle process for the synthesis (101-104) and the recycling (105-108) of an ionic liquid hydrogen storage based on the trimethyl-isopropyl-ammonium cation.

According to FIG. 1, a water soluble trimethylisopropylammonium salt produced by any quaternization reaction—e.g. a halide made from trimethylamine and 2-halopropane, or preferably a methylcarbonate via the so called carbonate route (preferably because of being free of any corrosive halides, see e.g. WO 2005/021484, WO 2008/052863, WO 2008/052860)—is dissolved together with a boroyhdride e.g. sodium borohydride and a homogenous aqueous solution (101) is formed. $Y^-$ is any anion which is able to form a water soluble salt with the trimethyl-iso-propylammonium cation, preferably $CH_3CO_3$, $RCO_3^-$, $Cl^-$, $Br^-$, $I^-$, $RSO_4^-$, $R_2PO_4^-$ with R=C1-C4 alkyl, most preferably $CH_3CO_3^-$, $RCO_3^-$. It is preferred to use a limited amount of water, e.g. just the necessary amount to dissolve all components such, that a concentrated solution is formed. A phase separation inducer $A^+B^-$ is added (102): $A^+$ is a cation and $B^-$ is an anion and $A^+B^-$ is any organic or inorganic salt which strongly coordinates to water and does not react with the borohydride or the quaternary trimethylisopropylammonium salt. By forming hydrogen bonds with water, $A^+B^-$ withdraws solvation power of the water from the reaction systems to induce an ion exchange process followed by phase separation (salting out), whereupon the more hydrophobic borohydride anion combines with the trimethylisopropylammonium cation and the more hydrophilic anion $Y^-$ combines with the sodium cation. After phase separation an aqueous solution of $A^+B^-$ and $Na^+Y^-$ (104) can be separated from the desired trimethylisopropylammonium borohydride, which forms a stable, homogenous aqueous solution (103), e.g. a concentration of >50% by weight typically has been found to be stable.

The solution obtained can be contacted with special types of catalysts to form hydrogen gas just in time and quantity needed by controlling the flow through the catalyst-cell (105), e.g. analogously as described in WO 2010/081657.

Trimethyl-iso-propylammonium borohydride ($TMiPA^+ BH_4^-$) releases hydrogen according to the equation

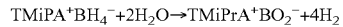

$$TMiPA^+BH_4^- + 2H_2O \rightarrow TMiPrA^+BO_2^- + 4H_2$$

theoretically up to 6.8% weight of hydrogen, this corresponds to 5.2% weight of hydrogen including the mass of the 2 equivalents water, in reality somewhat lower due to a needed excess of water to keep the system liquid. In contrast to the procedures of WO 2010/081657 the solution prepared according to the present invention is homogeneous, already contains the water needed for the reaction and reacts with higher kinetic, since only one phase has to contact the catalyst's surface and not two, as is the case with the emulsion described in WO 2010/081657.

After the release of hydrogen the storage material has been converted into its unloaded trimethyl-iso-propylammonium metaborate form and is still in homogenous solution. For the following recycling step (analog to 101-104) a borohydride e.g. sodium borohydride and optionally as less as possible water is added (106) and then phase separation is induced by adding the phase separation inducer $A^+B^-$, forming the recycled trimethylisopropylammonium borohydride solution (107) and a separated solution containing sodium metaborate and the phase separation inducer (108).

Sodium metaborate is a known starting material for the synthesis of sodium borohydride; this procedure (109) therefore closed the overall recycling process.

There are different strategies to proceed as described in the literature, see e.g.

Park, Eun Hee; Jeong, Seong Uk; Jung, Un Ho; Kim, Sung Hyun; Lee, Jaeyoung; Nam, Suk Woo; Lim, Tae Hoon; Park, Young Jun; Yu, Yong Ho; International Journal of Hydrogen Energy (2007), 32(14), 2982-2987.

Minkina, Valentina; Banal, Katia; F R 2870534 A1 20051125.

Cakanyildirim, Cetin; Guru, Metin; International Journal of Hydrogen Energy (2008), 33(17), 4634-4639

Saitoh, Yasuo; Yoshizaki, Atsuhiro; Ibaraki Kogyo Koto Senmon Gakko Kenkyu Iho (2009), 44, 47-54.

Saito, Yasuo; Hirata, Keiichi; Ando, Mamoru; Jpn. Kokai Tokkyo Koho (2010), JP 2010013290 A 20100121

Cakanyildirim, Cetin; Guerue, Metin; Renewable Energy (2010), 35(9), 1895-1899.

Kong, Lingyan; Cui, Xinyu; Wu, Jie; Jin, Huazi; Xiong, Tianying; Faming Zhuanli Shenqing Gongkai Shuomingshu (2010), CN 101654223 A 20100224.

Xiong, Tianying; Li, Tiefan; Wu, Jie; Jin, Huazi; Kong, Lingyan; Cui, Xinyu; Lv, Baojun; Faming Zhuanli Shenqing Gongkai Shuomingshu (2009), CN 101519188 A 20090902.

Bliesner, Wayne Thomas; U.S. Pat. Appl. Publ. (2011), US 20110100356 A1 20110505.

Li, Z. P.; Liu, B. H.; Zhu, J. K.; Morigasaki, N.; Suda, S.; Journal of Alloys and Compounds (2007), 437(1-2), 311-316.

Liu, Bin Hong; Li, Zhou Peng; Zhu, Jing Ke; Morigasaki, N.; Suda, S.; Energy & Fuels ACS ASAP Suda, S.; Morigasaki, N.; Iwase, Y.; Li, Z. P.; Journal of Alloys and Compounds (2005), 404-406 643-647.

Minkina, Valentina; Banal, Katia; F R 2870534 A1 20051125

Kojima, Yoshitsugu.; Chuo Kenkyusho R&D Rebyu (2005), 40(2), 31-36.

Chen, Rui.; WO 2004035464 A2

Kojima, Yoshitsugu; Haga, Tetsuya; International Journal of Hydrogen Energy (2003), 28(9), 989-993.

Morigasaki, Nobuto; Tanisawa, Kazuhiro; Li, Zhoupeng; Suda, Seijirau; Kogakuin Daigaku Kenkyu Hokoku (2002), 93 55-59.

Demirci, U. B.; Akdim, O.; Miele, P.; International Journal of Hydrogen Energy (2009), 34(6), 2638-2645

Bürchner, Mara; Erle, Anna M. T.; Scherer, Harald; Krossing, Ingo; Chem. Eur. J. (2012), in press; DOI: 10.1002/chem.2011102460.

The overall process is characterized by the controlled switching of the miscibility properties between homogeneous (one phase) and non-homogeneous (more than one phase) state and therefore prevent other costly and time consuming separation steps.

Figure 2:
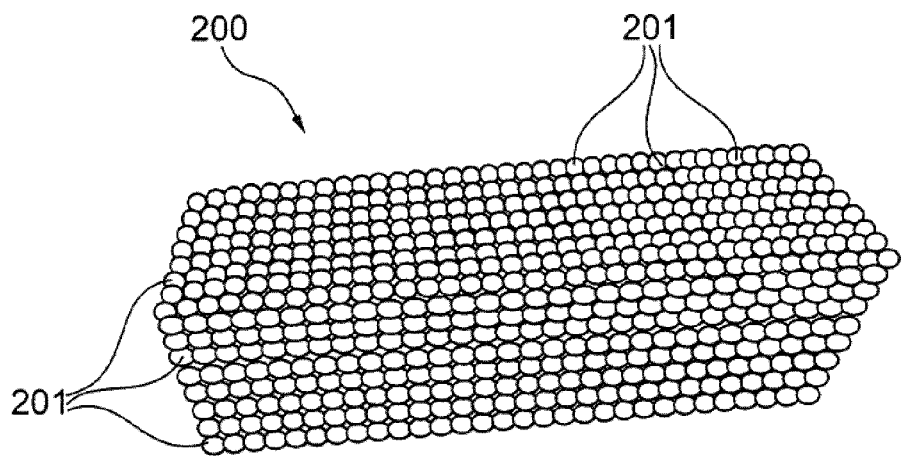
FIG. 2 schematically shows a catalytic converter comprising a catalyst material.

FIG. 2 schematically shows a possible form of a catalytic converter comprising a catalyst material. In general the catalytic converter 200 comprises or substantially consists of a noble metal, e.g. platinum or palladium, and has a height specific surface area and optionally nonporous morphology, e.g. to avoid mass transport problems, in order to facilitate a reaction, e.g. a release of hydrogen. In particular, the catalytic converter is formed of a plurality of small balls or spheres 201 having a diameter of about 1 mm to 2 mm. These spheres are formed to a structure having a hexagonal, cubic or face-centered cubic arrangement of the spheres. In particular, the arrangement should be as dense as possible to increase the surface the catalyst and the ionic liquid come into contact. The plurality of spheres may be sintered to form the catalytic converter 200. The single spheres 201 may be formed by sintering metal powder, wherein the powder particles have a size in the micrometer or nanometer range, e.g. between 1 nm and 50 micrometer, more particular in the range of 10 nm to 5 micrometer. Due to the fact that the catalytic converter comprises a plurality of balls or spheres the catalytic converter may adopt almost any desired form, e.g. may be cut to the desired form.

Figure 3:
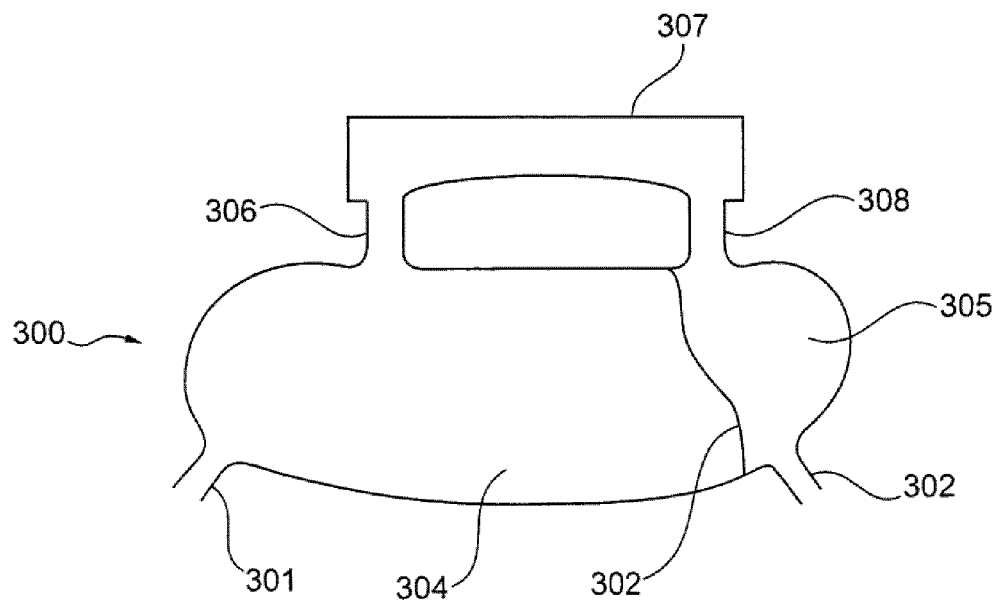
FIG. 3 schematically shows a container for storing a hydrogen storage medium.
Figure 4:
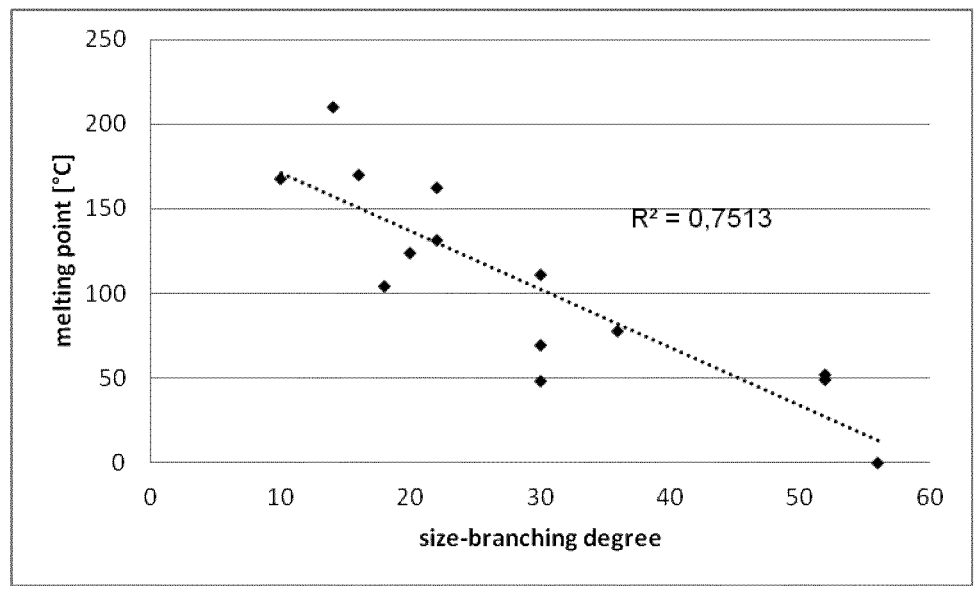
FIG. 4 schematically shows a correlation diagram between melting points of different tetraalkylammonium tetrahydroborates and their size-branching degree.

FIG. 3 schematically shows a container 300 for storing a hydrogen storage medium. In particular, the container 300 comprises an inlet 301, an outlet 302 and a moveable, elastic or flexible membrane 303 separating two chambers or portions of the container from each other. By using the inlet 301 a hydrogen rich ionic liquid, e.g. trimethyl-iso-propylammonium-BH4, may be supplied into the container filling the left chamber 304 in FIG. 3, while the outlet 302 may be used to discharge a hydrogen depleted ionic liquid, e.g. trimethyl-iso-propylammonium-BO2, from the right chamber 305 in FIG. 3. Furthermore, the container 300 comprises an output connection 306 arranged in the chamber 304 which is connected to an external housing 307 in which a catalytic converter is arranged. That is in the housing the hydrogen is released from the hydrogen rich ionic liquid and the hydrogen depleted ionic liquid is generated. Furthermore, the housing is connected to an input connection 308 of the container 301 which input connection is arranged in the chamber 305.

The aspects defined above and further aspects of the invention are apparent from the examples of embodiment to be described hereinafter and are explained with reference to these examples of embodiment. It should be noted that features described in connection with one exemplary embodiment or exemplary aspect may be combined with other exemplary embodiments and other exemplary aspects.

EXPERIMENTS

Example 1

Synthesis of 1-methyl-1-iso-butylpiperidinium borohydride

The synthesis consists of two reactions: alkylation of 1-methylpyrrolidine with 1-bromo-2-methylpropane to obtain 1-methyl-1-iso-butylpiperidinium bromide and following ion exchange of the latter with sodium borohydride.

Reaction 1: Preparation of 1-methyl-1-iso-butylpiperidinium bromide 7.663 g of 1-methylpyrrolidine together with 16.035 g of 1-bromo-2-methylpropane were transferred into a glass reactor with magnetic stirring equipment. The closed reactor was warmed up in the oil bath at 120° C. for 3 days and cooled down. Solid material was obtained, washed with an excess of petrol ether and taken up in isopropanole. From the mixture obtained solvent was removed and the residue obtained was dried at 70° C. under 10 mbar of vacuum for 3 hours.

18.42 g, ca. 92% of theory, of 1-methyl-1-iso-butylpiperidinium bromide was obtained.

Reaction 2: Preparation of 1-methyl-1-iso-butylpiperidinium borohydride 3.8 g of sodium hydroxide was dissolved in 15 g water, resulting in 18.8 g of strongly basic solution. Ca. 3 ml of this solution was added to an aqueous solution of 18.4 g of 1-methyl-1-iso-butylpiperidinium bromide in 10 g $H_2O$. The rest of the basic solution, was slowly added to 4.7 g of solid sodium borohydride, resulting in homogeneous solution of the latter. The solution containing sodium borohydride obtained was slowly added to the solution containing 1-methyl-1-iso-butylpiperidinium bromide under stirring. After addition, a sharp phase separation took place. The organic phase was collected and washed with 30 g water, resulting in the formation of one single homogeneous phase. To the mixture obtained 6 g of solid sodium hydroxide was added and a second phase (20.8 g) was formed. The latter was collected and dried (100° C., $10^{-2}$ mm. Hg., 2 hours). 11.9 g, ca. 91% of theory, of 1-methyl-1-iso-butylpiperidinium borohydride was obtained which contained 4% hydrogen (determined volumetrically). Theoretical capacity is 5.1%.

Example 2

Synthesis of trimethyl-iso-propylammonium borohydride

The synthesis consists of two reactions: methylation of dimethyl-iso-propylamine with dimethylcarbonate to obtain trimethyl-iso-propylammonium methylcarbonate and following ion exchange of the latter with sodium borohydride.

Reaction 1: Preparation of trimethyl-iso-propylammonium methylcarbonate 1000 g of dimethyl-iso-propylamine and 1343.5 g of dimethylcarbonate were dissolved in 1004.37 g of methanol. The mixture obtained was transferred into the high pressure reactor and purged with Ar under constant stirring at room temperature. After 20 min Ar flow was stopped and the temperature was set to 90° C. After 7 days >99.9% of conversion was obtained (proof by titration) and 3348 g of 60.3% solution of trimetyl-iso-propylammonium methylcarbonate in methanol was obtained.

To the solution obtained 1600 g of water was added with subsequent methanol removal under vacuum (90 mbar, 60° C.). 3424 g of an aqueous solution with 59.4% concentration of trimetyl-iso-propylammonium methylcarbonate was obtained and was used for further ion exchange reaction.

Reaction 2: Preparation of trimethyl-iso-propylammonium borohydride 207 g of an aqueous solution containing 50 g of sodium hydroxide and 157 g of water, was slowly added to 100 g of solid sodium borohydride under mechanical mixing.

626 g of an aqueous solution containing 30 g of sodium hydroxide and 596 g of water were added to 606.73 g of an aqueous solution (59.4 w. %) of 360.398 g of trimethyl-iso-propylammonium methylcarbonate. The solution obtained was slowly added to the solution of sodium borohydride, prepared as stated above.

When both solutions were mixed in the above described way, sharp phase separation occurred. The organic phase (900 g) obtained was collected and mixed with 500 g of water and one homogeneous phase was formed. To the mixture obtained 236.32 g of sodium hydroxide was added to induce phase separation again. Finally, the organic phase (382 g) was collected and dried under vacuum. 187 g of trimethyl-iso-propylammonium borohydride was obtained (corresponding to a yield of 79% of theory) having a hydrogen capacity of 7.4% (volumetric testing, theoretical capacity is 6.84%, the compound contains probably some amount of $NaBH_4$)). The preparation procedure described is not optimized.

Example 3

Preparation of trimethyl-iso-propylammonium metaborate 30 g of trimethyl-iso-propylammonium borohydride was dissolved in 60 g of water. The solution obtained had a volume of ca. 98-99 ml, i.e. a density of ca. 0.9 g/ml. No gas development was observed during this procedure.

To the solution obtained a commercial $Pt/Al_2O_3$ catalyst (1.3 g, 1 weight % Pt, 3.2 mm pellets) was added and strong gas development started. To accelerate gas development, ultrasonic and heat (60° C.) were applied. After gas development had stopped, the catalyst was removed via filtration and to the mixture obtained water was added. 123.9 g (120 ml) of a transparent homogeneous solution containing trimethyl-iso-propylammonium metaborate was obtained.

Example 4

Recycling of Organic Borohydride 256.3 mmol of trimethyl-iso-propylammonium metaborate in aqueous solution, prepared as described in Example 3, was used to prepare trimethyl-iso-propylammonium borohydride via ion exchange with sodium borohydride.

8.02 g of sodium hydroxide was dissolved in 16 g of water. The solution obtained was slowly added to 12.6 g of solid sodium borohydride under mechanical mixing. To the mixture obtained 10 g of water was added and the solution appeared to be homogeneous. The solution obtained was added to the solution containing trimethyl-iso-propylammonium metaborate under vigorous stirring and no gas development was observed. Stirring of the mixture obtained was terminated and two phases formed. To the system obtained 5 g of solid sodium hydroxide was added, however, without expected improvement. The phases were separated and the upper phase obtained was added to 30 g of water to form one phase. To the aqueous phase obtained 8.7 g of sodium hydroxide was added and two phases were formed. To the system obtained 3.9 g of sodium hydroxide was added without expected improvement. The upper phase was collected and dried under vacuum ($10^{-1}$ mm Hg. at 80° C. for 2 hours). 18 g of trimethyl-iso-propylammonium borohydride in the form of a white solid was obtained, having 7.6% of hydrogen capacity (volumetric test, theoretical capacity is 6.84%).

All synthesized product and some commercially available materials of the "Product Table" below were characterized in terms of melting point and decomposition temperature, with the help of standard TGA/DSC analysis under flow of air and the hydrogen storage capacity was measured by gas volumetric analysis. The TGA/DSC instrument from NETZSH (STA 449C Jupiter) was used in determination of melting point and decomposition temperature. The following set of parameters was used: Air flow: 20 ml/min, temperature ramp=5° K/min from 30° C. till 1000° C. The temperature and DSC signals were calibrated before measurements. The so called "correction run" was made with two empty cruccibles to minimize the buoyancy effect.

PRODUCT TABLE

| Entry | Cation | Size-branching degree[a] | M.W. Cation [g/mol] | $T_{melting}$ [° C.] | Theory[b] $H_2$ [% w] | Exp. $H_2$ [% w] |
|---|---|---|---|---|---|---|
| 2 | [structure] | 30 | 214.36 | 48 | 3.5 | 2.1 |
| 3 | [structure] | 56 | 298.56 | 0 | 2.6 | 2.6 |
| 4 | [structure] | 52 | 353.66 | 52 | 2.2 | 1.6 |
| 5 | [structure] | 22 | 142.26 | 162 | 5.1 | 5.2 |

PRODUCT TABLE-continued

| Entry | Cation | Size-branching degree[a] | M.W. Cation [g/mol] | $T_{melting}$ [°C.] | Theory[b] $H_2$, [% w] | Exp. $H_2$, [% w] |
|---|---|---|---|---|---|---|
| 6 | (N-methyl-isobutyl-pyrrolidinium) | 22 | 142.26 | 131 | 5.1 | 4.0 |
| 7 | (N-methyl-octyl-pyrrolidinium) | 30 | 198.36 | 111 | 3.8 | 2.0 |
| 8 | (N-methyl-(3-ethylhexyl)-pyrrolidinium) | 30 | 198.36 | 69 | 3.8 | 1.1 |
| 9 | (cyclohexyl-dimethyl-(2-ethylhexyl)-ammonium) | 36 | 240.46 | 78 | 3.1 | 2.0 |
| 10 | (N-ethyl-N-methyl-morpholinium) | 20 | 130.20 | 124 | 5.5 | 5.4 |
| 11 | (N-methyl-ethyl-pyrrolidinium) | 16 | 100.18 | >170 | 7.0 | 6.2 |
| 12 | (isopropyl-trimethyl-ammonium) | 14 | 102.19 | >210 | 6.8 | 6.98 |
| 13 | (N,N-dimethyl-morpholinium) | 18 | 116.18 | — | 6.11 | 6.14 |
| 14 | $N^+(C_2H_5)_4$ | 18 | 130.25 | 104 | 5.51 | 5.47 |
| 15 | $N^+(CH_3)_4$ | 10 | 74.05 | 168 | 8.99 | 8.93 |

[a] The size-branching degree was defined as $1 \cdot C_1 + 2 \cdot C_2 + 3 \cdot C_3 + 6 \cdot C_4$, where $C_1$ - number of primary carbon atoms, $C_2$ - number of secondary carbon atoms, $C_3$ - number of tertiary carbon atoms and $C_4$ - number of quaternary carbon atom. Please note, that the heteroatoms were considered as carbon atoms for convenience.
[b] After $Q^+BH_4^- + 2H_2O \rightarrow Q^+BO_2^- + 4H_2$, $Q^+$ denoting the corresponding cation, 2 moles of water not included.

The invention claimed is:

1. A method of storing and releasing hydrogen with a borohydride/borate system, comprising:
   providing, in a homogeneous aqueous solution, a first water-miscible ionic liquid that includes a borohydride anion with releasable hydrogen and a cation,
   releasing hydrogen out of the first ionic liquid by contacting the homogeneous aqueous solution with a catalyst to form a second water-miscible ionic liquid comprising a borate anion and the cation from the first ionic liquid in a second homogeneous solution
   treating the second ionic liquid with an amount of regenerative borohydride salt to regenerate the first ionic liquid and form an aqueous mixture comprising the regenerated first ionic liquid and a borate salt,
   separating the regenerated first ionic liquid from the aqueous mixture by adding an amount of a phase separation inducer, in addition to the amount of regenerative borohydride salt used to regenerate the first ionic liquid, to form a first phase containing the regenerated first ionic liquid and a second phase containing water, the phase separation inducer, and the borate salt, and
   recovering the regenerated first ionic liquid by separating the first phase from the second phase.

2. The method according to claim 1, wherein the cation of the first and second ionic liquids is a quaternary or protonated cation.

3. The method according to claim 1, wherein the cation of the first and second ionic liquids comprises one to four moieties selected from the group consisting of hydrogen, C1-C8-alkyl, C2-C8-alkenyl, C2-C8-alkinyl, C3-C8-cycloalkyl, C3-C8-cycloalkenyl, C5-C6-aryl, and C5-C6-heteroaryl.

4. The method according to claim 1, wherein the cation of the first and second ionic liquids is selected from pyridinium, pyrrolium, ammonium, phosphonium, piperidinium, pyrrolidinium, morpholinium, imidazolium, and pyrazolium.

5. The method according to claim 1, wherein the phase separation inducer is at least one of a hydroxide, carbonate, alkylcarbonate, borohydride salt, or metaborate salt.

6. The method according to claim 1, wherein the phase separation inducer comprises an additional quantity of the cation in the second ionic liquid.

7. The method according to claim 1, wherein the phase separation inducer comprises an additional quantity of the borate anion in the second ionic liquid.

8. The method according to claim 1, wherein the catalyst is a transition metal and/or a noble metal.

9. The method according to claim 1, wherein the first ionic liquid and/or the second ionic liquid has a viscosity value below 100 mPa at room temperature and/or below 2000 mPa at −20° C.

10. The method according to claim 9, wherein a viscosity level is set to the viscosity value by adding an additive.

11. The method according to claim 10, wherein the additive is selected from the group consisting of: amide, ether, including cyclic or polyether, acetals, ketals, alcohols, including polyalcohols, aromatic hydrocarbons, aliphatic hydrocarbons, dibutylethers, diethylethers, methyl tert-butyl ethers, ethyl tert-butylethers, 1,2-diethoxyethanes, formaldehyde dimethylacetales, polyethylene glycol dimethylethers, polyvinyl alcohols, and water.

12. The method according to claim 1, further comprising adding a basic additive to the first ionic liquid and/or the second ionic liquid.

13. The method according to claim 1, wherein the first ionic liquid further comprises inorganic borohydride selected from $NaBH_4$, $KBH_4$ and/or $LiBH_4$.

14. The method according to claim 1, wherein the cation of the first and second ionic liquids is selected from ammonium, pyrrolidinium, morpholinium, and piperidinium.

15. The method according to claim 1, wherein the cation of the first and second ionic liquids is selected from pyridinium, pyrrolium, imidazolium, and pyrazolium.

16. The method according to claim 1, wherein the cation of the first and second ionic liquids is phosphonium.

17. The method according to claim 8, the transition metal and/or a noble metal forming a microcrystalline or nanocrystalline structure.

18. A method of storing and releasing hydrogen within a borohydride/borate system, the method comprising:
providing a first ionic liquid as a homogeneous aqueous solution, the first ionic liquid comprising a borohydride anion with releasable hydrogen and a cation;
releasing hydrogen out of the first ionic liquid by contacting the homogenous aqueous solution with a catalyst, the release of hydrogen from the first ionic liquid forming a second ionic liquid including a borate anion and the cation from the first ionic liquid in a second homogeneous aqueous solution;
regenerating the first ionic liquid by treating the second ionic liquid with an amount of borohydride salt to form an aqueous mixture comprising the regenerated first ionic liquid and a borate salt, wherein: the first ionic liquid and the second ionic liquid are both water miscible;
(ii) adding a phase separation inducer to the aqueous mixture to induce separation of the first ionic liquid as a separate phase from the aqueous mixture, the phase separation inducer including a salt which coordinates to the water in the aqueous mixture and does not react with the borohydride, wherein the phase separation inducer is selected from the group consisting of hydroxide salt, carbonate salt, chloride salt, sulfate salt, phosphate salt, carboxylate salt, an amount of borate salt in addition to the borate salt formed when regenerating the first ionic liquid, an amount of borohydride salt in addition to the borohydride salt used to regenerate the first ionic liquid, and combinations thereof; and
separating the regenerated first ionic liquid from the borate salt and the phase separation inducer.

19. A method of storing and releasing hydrogen within a borohydride/borate system, the method comprising:
providing a first ionic liquid as a homogeneous aqueous solution, the first ionic liquid comprising a borohydride anion with releasable hydrogen and a cation;
releasing hydrogen out of the first ionic liquid by contacting the homogenous aqueous solution with a catalyst, the release of hydrogen from the first ionic liquid forming a second ionic liquid including a borate anion and the cation from the first ionic liquid in a second homogeneous aqueous solution;
regenerating the first ionic liquid by treating the second ionic liquid with an amount of regenerative borohydride salt to form an aqueous mixture comprising the regenerated first ionic liquid and a borate salt, wherein: the first ionic liquid and the second ionic liquid are both water miscible; and
adding a phase separation inducer, in addition to the amount of regenerative borohydride salt used to regenerate the first ionic liquid, to the aqueous mixture to induce separation of the first ionic liquid as a separate phase from the aqueous mixture,
wherein the regenerated first ionic liquid further comprises inorganic borohydride to an extent that the first regenerated ionic liquid remains water miscible and the second ionic liquid after the release of hydrogen from the first ionic liquid, remains water miscible and are present within the aqueous mixture.

20. The method of claim 19, wherein the phase separation inducer is selected from the group consisting of: alkaline metal hydroxides, alkaline metal carbonates, tetraalkylammonium hydroxides, tetraalkylammonium carbonates, tetraalkylphosphonium hydroxides, tetraalkylphosphonium carbonates, alkylcarbonates, an amount of borate salt in addition to the borate salt formed when regenerating the first ionic liquid, an amount of borohydride salt in addition to the borohydride salt used to regenerate the first ionic liquid, and combinations thereof.

* * * * *